United States Patent [19]

Chester et al.

[11] Patent Number: 5,243,112
[45] Date of Patent: Sep. 7, 1993

[54] LUBRICANT RANGE HYDROCARBONS FROM LIGHT OLEFINS

[75] Inventors: Arthur W. Chester, Cherry Hill, N.J.; Francis G. Dwyer, West Chester, Pa.; William E. Garwood, Haddonfield, N.J.; James C. Vartuli, West Chester, Pa.

[73] Assignee: Mobil Oil Corp., Fairfax, Va.

[21] Appl. No.: 776,247

[22] Filed: Sep. 16, 1985

Related U.S. Application Data

[63] Continuation-in-part of Ser. No. 373,451, Apr. 30, 1982, abandoned, and a continuation-in-part of Ser. No. 695,609, Jan. 28, 1985.

[51] Int. Cl.$^5$ ............................................. C07C 2/12
[52] U.S. Cl. ................................. 585/12; 585/18; 585/533
[58] Field of Search .......................... 585/533, 12, 18

[56] References Cited

U.S. PATENT DOCUMENTS

| | | | |
|---|---|---|---|
| 4,481,177 | 11/1984 | Valyosik | 423/329 |
| 4,482,772 | 11/1984 | Tabak | 585/254 |
| 4,520,221 | 5/1985 | Chen | 585/517 |
| 4,556,477 | 12/1985 | Dwyer | 208/111 |
| 4,574,043 | 3/1986 | Chester et al. | 208/111 |
| 4,605,488 | 8/1986 | Chester et al. | 208/111 |
| 4,717,465 | 1/1989 | Chen et al. | 208/59 |
| 4,783,555 | 11/1989 | Atkins | 502/77 |
| 4,810,357 | 3/1989 | Chester et al. | 208/97 |
| 4,814,543 | 3/1989 | Chen et al. | 585/739 |
| 4,902,406 | 2/1990 | Valyocik | 208/118 |
| 4,919,788 | 4/1990 | Chen et al. | 208/49 |
| 5,063,038 | 11/1991 | Kirker et al. | 502/77 |
| 5,135,638 | 8/1992 | Miller | 585/739 |
| 5,137,194 | 10/1992 | Rahmim et al. | 585/671 |

FOREIGN PATENT DOCUMENTS 0065400 8/1982 European Pat. Off.
0057049 11/1982 European Pat. Off.

Primary Examiner—Asok Pal
Attorney, Agent, or Firm—Alexander J. McKillop; Dennis P. Santini; Edward F. Kenehan, Jr.

[57] ABSTRACT

Lower olefins are upgraded to high viscosity index lubricants by converting olefinic feed over a medium pore zeolite catalyst consisting essentially of aluminosilicate HzSM-22 under oligomerization conditions.

11 Claims, No Drawings

LUBRICANT RANGE HYDROCARBONS FROM LIGHT OLEFINS

REFERENCE TO COPENDING APPLICATION

This application is a Continuation-in-part of U.S. patent applications Ser. No. 373,451, filed 30 April, 1982, now abandoned, and Ser. No. 695,609, filed 28 January, 1985, incorporated herein by reference.

FIELD OF THE INVENTION

This invention relates to a technique for the manufacture of high viscosity index lubricant range hydrocarbons. In particular, it provides an improved olefins conversion process and product. A novel oligomerization catalyst, comprising a shape selective medium pore silicate having a crystalline zeolite structure, is employed for upgrading olefinic feedstocks containing alkenes at elevated temperature and pressure.

BACKGROUND OF THE INVENTION

Recent work in the field of olefin upgrading has resulted in a catalytic process for converting lower olefins to heavier hydrocarbons. Heavy distillate and lubricant range hydrocarbons can be synthesized over ZSM-5 type catalysts at elevated temperature and pressure to provide a product having substantially linear molecular conformations due to the shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Particular interest is shown in a technique developed by Garwood, et al., as disclosed in European Patent Application No. 83301391.5, published 29 Sep. 1983. In U.S. Pat. Nos. 4,150,062; 4,211,640 and 4,227,992 Garwood et al disclose the operating conditions for a process for selective conversion of olefins to mainly aliphatic hydrocarbons.

In the process for catalytic conversion of olefins to heavier hydrocarbons by catalytic oligomerization using a medium e selective acid crystalline zeolite, process conditions can be varied to favor the formation of hydrocarbons of varying molecular weight. At moderate temperature and relatively high pressure, the conversion conditions favor $C_{20}^{+}$ aliphatic product. Lower olefinic feedstocks containing $C_2$-$C_8$ alkenes may be converted; however, the low severity conditions may not convert a major amount of ethylene. A typical reactive feedstock consists essentially of $C_3$-$C_6$ mono-olefins, with varying amounts of nonreactive paraffins and the like being acceptable components.

It is a main object of this invention to provide an improved process for upgrading olefins to valuable lubricant quality product. Significantly improved linearity can be achieved by employing a novel catalyst comprising a medium pore shape selective siliceous zeolite.

SUMMARY OF THE INVENTION

A novel synthesis process has been discovered for producing lubricant range hydrocarbons by oligomerizing lower olefin feed at elevated temperature and pressure which comprises contacting the lower olefin under oligomerization conditions with a medium pore shape-selective siliceous zeolite catalyst comprising a crystalline zeolite with the significant lines in its X-Ray diffraction pattern tested in Table 1, designated herein ZSM-22.

In the production of lubes from the reaction of olefins over the zeolitic catalyst designated herein ZSM-22 has been found to convert propylene to a high viscosity index, low pour lube oil. The VI obtained using the zeolite of this invention is higher than that obtained with ZSM-5.

DESCRIPTION OF THE PREFERRED EMBODIMENTS

The shape-selective oligomerization/polymerization catalyst preferred for use herein consists essentially of a crystalline aluminosilicate zeolite having a silica to alumina molar ratio of at least 20, a constraint index of about 1 to 12 (preferably about 2.5 to 3) and alpha activity of about 50–300. A suitable shape selective medium pore catalyst for fixed bed is a small crystal H-ZSM-22 zeolite (silica:alumina ratio=about 80:1) with alumina binder in the form of cylindrical extrudates of about 1–5mm. Unless otherwise stated in this description, the catalyst shall consist essentially of acidic ZSM-22 having a crystallite size of about 2–4 microns. In addition to the preferred alumino-silicate zeolites, other crystalline metallosilicates having tetrahedrally bound metals, such as gallosilicates, ferrosilicates, borosilicates or mixed Al, Ga, Fe, B in the framework may be employed. These siliceous materials can be synthesized to have pore size and x-ray diffraction characteristics of the aluminosilicate crystalline zeolite and provide the active Bronsted acid sites. Related materials are disclosed in European Patent Applications 57049, 65400 and 55045, incorporated by reference.

The preferred zeolite of the present invention contains a relatively minor amount of $Al_2O_3$ and can produce a product with a $SiO_2$ to $Al_2O_3$ mole ratio of about 20 to 1000 or more. In the as-synthesized form, the zeolite may have a calculated composition, in terms of moles of oxides, after dehydration, per 100 moles of silica, as follows:

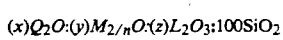

$$(x)Q_2O:(y)M_{2/n}O:(z)L_2O_3:100SiO_2$$

wherein $Q_2O$ is the oxide form of an organic compound containing an element of Group V-B (as defined in the IUPAC Periodic chart of the Elements), e.g., N or P, preferably N, containing at least one alkyl or aryl group having at least 2 carbon atoms, M is an alkali metal or an alkaline earth metal having a valence n, and wherein $x=0.01$–$2.0$, $y=0$–$2.0$, $z=0$–$5$, and L is a tetrahedrally bound atom selected from Al, Ga, Fe, B or mixtures thereof.

The zeolite herein designated as ZSM-22 can further be identified by its sorptive characteristics and its X-ray diffraction pattern. The original cations of the as-synthesized zeolite may be replaced at least in part by other ions using conventional ion exchange techniques. It may be necessary to precalcine the zeolite crystals prior to ion exchange. The replacing ions introduced to replace the original alkali, alkaline earth and/or organic cations may be any that are desired so long as they can pass through the channels within the zeolite crystals. Desirable replacing ions are those of hydrogen, rare earth metals, metals of Groups IIIA, IIIB, IVA, IVB and VIII. Among the metals, those particularly preferred are Group VIIIA of the IUPAC Periodic chart of the Elements, particularly Ni, Co or Pd.

The aluminosilicate zeolite described herein has a definite X-ray diffraction pattern, the significant lines of which are set forth below in Table I, which distinguishes it from other crystalline materials.

TABLE I

Most Significant Lines of the Zeolite Designated As ZSM-22

| Interplanar d-spacings (A) | Relative Intensity (I/Io) |
|---|---|
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and a associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in A, corresponding to the recorded lines, were determined. In Table I, the relative intensities are given in terms of the symbols vs=very strong, s =strong, s=strong, m=medium, w=weak, etc. This X-ray diffraction pattern is characteristic of all the species useful in this invention. Ion exchange of the alkali metal cations with other ions results in a zeolite which exhibits substantially the same X-ray diffraction pattern with some minor shifts in interplanar spacing and variation in relative intensity. Other minor variations can occur, depending on the silica to alumina ratio of the particular sample, as well as its degree of thermal treatment.

One suitable method for preparing the siliceous zeolite can be from a reaction mixture containing a source of silica, an alkane diamine, an alkali metal oxide or an alkaline earth metal oxide, e.g., sodium, potassium, cesium, calcium or strontium, water, and alumina, and having a composition, in terms of mole ratios of oxides, falling within the following ratios:

| Reactants | | Broad | Preferred |
|---|---|---|---|
| $SiO_2/Al_2O_3$ | = | 20 to ∞ | 30 to 100 |
| $H_2O/SiO_2$ | = | 10 to 100 | 20 to 60 |
| $OH^-/SiO_2$ | = | 0 to 0.3 | 0.1 to 0.2 |
| $M^+/SiO_2$ | = | 0 to 2.0 | 0.1 to 1.0 |
| $RN/SiO_2$ | = | 0.01 to 2.0 | 0.05 to 1.0 | wherein RN is a $C_2$-$C_{12}$ alkane diamine of the formula $H_2N$—$(CH_2)_n$—$NH_2$ (abbreviated $C_nDN$), n=2 to 12, and preferably is 5 to 8, and M is an alkali metal or an alkaline earth metal and maintaining the mixture at crystallization temperature until crystals of the zeolite are formed. Thereafter, the crystals are separated from the liquid by an conventional means, washed and recovered.

Shape-selective oligomerization, as it applies to the conversion of $C_2$-$C_{10}$ olefins over the zeolite herein designated as ZSM-22, can produce higher olefins up to $C_{30}$ and higher. As reported by Garwood in Intrazeolite Chemistry 23, (Amer. Chem. Soc., 1983), ZSM-5-catalyzed reaction conditions favoring higher molecular weight product are low temperature (200°-260° C.), elevated pressure (about 2000 kPa or greater), and long contact time (less than 1 WHSV). The reaction under these conditions proceeds through the Bronsted acid-catalyzed steps of (1) oligomerization, (2) isomerization-cracking to a mixture of intermediate carbon number olefins, and (3) interpolymerization to give a continuous boiling product containing all carbon numbers. The channel systems of the shape selective catalysts impose constraints on the configuration of the large molecules, accounting for the differences with other catalysts.

The following model reaction path for propylene is set forth for purposes of explanation, and it should be taken as a theoretical path, as the process is presently understood by workers in the field.

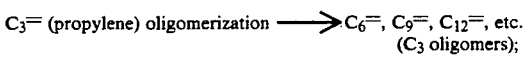

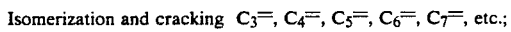

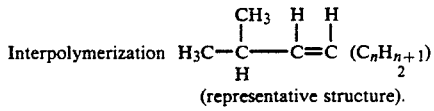

The desired oligomerization-polymerization products include $C_{20}^+$ substantially linear aliphatic hydrocarbons. The ZSM-22 catalytic path for alkene feed is believed to provide a long chain, possibly with lower alkyl (e.g., methyl) substituents in the straight chain. After hydrofinishing, the lubricant range final product can be characterized as a typical linear molecule having a sparingly-substituted saturated long carbon chain.

The final molecular conformation is influenced by the pore structure of the catalyst. For the higher carbon numbers, the structure is primarily a methyl-branched straight olefinic chain, with the maximum cross section of the chain limited by the dimension of the largest ZSM-22 pore. Although emphasis is placed on the normal 1-alkenes as feed stocks, other lower olefins such as 2-butene or isobutylene, are readily employed as starting materials due to rapid isomerization over the acidic zeolite catalyst. At conditions chosen to maximize heavy distillate and lubricant range products ($C_{20}^+$ the raw aliphatic product is essentially mono-olefinic.

The viscosity index of a hydrocarbon lube oil is related to its molecular conformation. Extensive branching in a molecule usually results in a low viscosity index. It is believed that two modes of oligomerization/polymerization of olefins can take place over medium pore acidic zeolites. One reaction sequence takes place at Brönsted acid sites inside the channels or pores, producing essentially linear materials. The other reaction sequence occurs on the outer surface, producing highly branched material. By decreasing the surface acid activity of such zeolites, fewer highly branched products with low VI are obtained.

Several techniques may be used to increase the relative ratio of intra-crystalline acid sites to surface active sites. This ratio increases with crystal size due to geometric relationship between volume and superficial surface area. Deposition of carbonaceous materials by coke formation can also shift the effective ratio, as displayed in copending U.S. patent application Ser. No. 629,371 of Garwood et al, filed Jul. 10, 1984 now U.S. Pat. No. 4,547,613 and incorporated by reference. Enhanced effectiveness is observed where the surface acid sites of small crystal zeolites are reacted with a chemisorbed organic base or the like.

Catalysts of low surface activity can be obtained by using medium pore zeolites of small crystal size that have been deactivated by basic compounds, examples of which are amines, phosphines, phenols, polynuclear hydrocarbons, cationic dyes and others. Those amines with an effective cross section larger than about 5 Angstroms are suitable especially substituted quinolines, heterocyclic amines and alkyl-substituted pyridines such as 2,4 or 2,6-di-alkyl pyridines. Preferred are bulky, sterically-hindered di-ortho-alkyl pyridines, such as 2,6-di-tertiary-butylpyridine. Other surface deactivating techniques are disclosed by Chen in U.S. Pat. No. 4,520,221.

The catalysts may be treated with organic silicon compounds, as described in U.S. Pat. Nos. 4,100,215 and 4,002,697 to impart the desired degree of surface deactivation while being essentially free of carbonaceous deposits. Such treatment involves contacting the catalyst with a silane surface modifying agent capable of deactivating catalytic (acidic) sites located on the external surface of the zeolite by chemisorption.

Conventional temperatures, pressures and equipment may be used in the novel process disclosed herein. Preferred temperatures may vary from about 100° to about 350° C., preferably 150° to 250° C. pressures from about atmospheric to 20,000 kPa (3000 psi) and WHSV from about 0.01 to about 2.0, preferably 0.2 to 1.0 are employed.

In a typical continuous process run under steady state conditions using this zeolite catalyst, the average reactor temperature in the series of adiabatic fixed bed reactors is maintained below about 260° C. (500° F.). In order to optimize formation of high molecular weight $C_{20}+$ hydrocarbons maximum temperature from the terminal reactor is kept below about 290° C. (550° F.).

The reactor effluent liquid stream is fractionated to provide a raw product stream consisting essentially of 315° C.+ aliphatic hydrocarbons, comprising a major amount of heavy distillate and lubricant range $C_{20}$–$C_{60}$ aliphatic hydrocarbons. This raw olefinic product may then be hydrotreated in a separate process step to provide a paraffinic lubricant and/or heavy distillate product. Details of a mild hydrogenation treatment may be obtained from U.S. Pat. No. 4,211,640, incorporated by reference, typically using Co or Ni with W/Mo and/or noble metals. The hydrotreated stream may be further fractionated to yield refined high grade lubricants of outstanding quality.

EXAMPLE 1

Zeolite Synthesis and Catalyst Preparation

A solution is prepared by mixing one part (by wt.) aluminum sulfate, 4.5 parts potassium hydroxide (86% by wt.) and 50 parts water. This solution is added to an autoclave. Another solution is prepared by mixing 27.6 parts colloidal silica (30% by wt.) and 36 parts water and then this mixture is added to the autoclave. Six parts of diethylamine hydrochloride are then added and the combined solution is agitated vigorously for approximately one-half hour. The autoclave is heated to about 165° C. (330° F.) with constant stirring and maintained for 72 hours at this temperature. The resultant crystalline material is then filtered and washed on a Buchner funnel and then dried overnight at about 120° C. (250° F.). The x-ray diffraction analysis results in the pattern given in Table I. Chemical analysis gave a silica to alumina molar ratio of 82.

This zeolite is mixed with alpha-$Al_2O_3.H_2O$ to make a catalytic mixture of 65 parts zeolite and 35 parts alumina. Enough water is added to the mixture so that the resulting catalyst could be formed into 1½ mm extrudates. These extrudates are activated by first calcining in nitrogen at 1000° F., followed by aqueous exchanges with a 1.0 N ammonium nitrate solution and finally calcining in air at 1000° F. The alpha value of this zeolite is 57.

In the following examples the experiments are conducted with propylene charge at 1500 psig, 0.5 WHSV charging the propylene as a liquid continuously with a positive displacement pump in a high pressure fixed bed reactor. The catalysts are extrudates, as described, containing 35 wt% alumina binder. The catalysts were sized to 14–25 mesh, and purged in situ with hydrogen at about 480° C. and atmospheric pressure for one hour to ensure a standard dried condition before introduction of the olefin.

EXAMPLE 2

Propylene is continuously charged over the catalyst of example 1 for a total of four days, the first two days at an average catalyst temperature of about 200° C. (395° F.) and the last two days at about 235° C. (450° F.). Liquid product recovery is 96 wt Distillation of the liquid product gives 21 wt % bottoms lubricant fraction (based on propylene charge) boiling at about 315° C. (600° F.) and having the properties shown in Table II.

EXAMPLE 3

Propylene is passed over a commercial preparation of HZSM-5 $SiO_2/Al_2O_3 = 70/1$ extrudate having an alpha value of 180 for a total of three days, the first two at an average catalyst temperature of about 235° C. (420° F.) and the third at about 240° C. (460° F.). Liquid recovery is 96 wt %. Distillation of the liquid product gives a bottoms lube fraction having the properties shown in Table II.

TABLE II

|  | Ex. 2 | Ex. 3 (ZSM-5) |
| --- | --- | --- |
| Cut Point | 315° C. | 315° C. (600° F.) |
| Lube Yield, wt % (1) | 21 | 18 |
| Gravity, |  |  |
| °API | 37.6 | 35.3 |
| Specific | 0.8368 | 0.8483 |
| Pour Point | −54° C. | −46° C. |
| K.V. @ 40° C., cs | 9.83 | 27.28 |
| K.V. @ 100° C., cs | 2.57 | 4.62 |
| V.I | 85.7 | 73.4 |

(1) Based on propylene charge

While the invention has been described by reference to particular examples, there is no intent to limit the inventive concept, except as set forth in the following claims.

It is claimed:

1. A synthesis process for producing lubricant range hydrocarbons by oligomerizing lower olefin feed at elevated temperature and pressure which comprises contacting the lower olefin under oligomerization conditions with a medium pore shape-selective siliceous zeolite catalyst consisting essentially of aluminosilicate HZSM-22.

2. The process of claim 1 including the step of separating the reaction product to obtain a heavy fraction rich in substantially linear C20+ olefins.

3. The process of claim 2 wherein lubricant range hydrocarbons boiling above 315° C. have a viscosity index of at least about 85.

4. The process of claim 1 wherein the olefinic feed comprises $C_2$-$C_8$ olefins; the catalyst comprises aluminosilicate having a silica-to-alumina mole ratio of at least 20 and a constraint index of about 2.5 to 3.

5. The process of claim 1 wherein the olefinic feed consists essentially of $C_3$-$C_4$ aliphatics; the catalyst consists essentially of a fixed bed of zeolite catalyst particles having an acid cracking value prior to deactivation treatment of about 50 to 300, and the process is conducted at a temperature of about 150° C. to 290° C., a pressure of at least about 1500 kPa and weight hourly space velocity of about 0.1 to 2 $hr^{-1}$.

6. In the process for upgrading lower olefins to produce lubricant range hydrocarbons by controlling olefinic feed comprising $C_2$-$C_8$ alkene with a shape selective medium pore acidic zeolite oligomerization catalyst at high pressure and moderate temperature, the improvement wherein said zeolite catalyst comprises ZSM-22 having, as synthesized, a calculated composition, expressed in terms of moles of anhydrous oxides, as follows:

(y)$M_{2/n}$:(z)$L_2O_3$:100$SiO_2$; M is an alkali or alkaline earth metal having a valence n, y=0 to 2.0, z=0 to 5, and L is a tetrahedrally bound atom selected from Al, Ga, Fe, B or mixtures thereof.

7. In the process of claim 6 wherein said zeolite catalyst has an X-ray diffraction substantially as set forth in Table I below:

TABLE I

| Interplanar spacings d(A°) | Relative Intensity I/Io |
|---|---|
| 10.9 ± 0.2 | medium-very strong |
| 8.7 ± 0.16 | weak |
| 6.94 ± 0.10 | weak-medium |
| 5.40 ± 0.08 | weak |
| 4.58 ± 0.07 | weak |
| 4.36 ± 0.07 | very strong |
| 3.68 ± 0.05 | very strong |
| 3.62 ± 0.05 | strong-very strong |
| 3.47 ± 0.04 | medium-strong |
| 3.30 ± 0.04 | weak |
| 2.74 ± 0.02 | weak |
| 2.52 ± 0.02 | weak |

8. In the process of claim 7 wherein said zeolite ZSM-22 consists essentially of an acidic aluminosilicate.

9. A process for converting lower olefins to lubricant-grade hydrocarbons comprising contacting an olefinic feedstock with a siliceous zeolite in a reactor under such temperature and pressure conditions to convert at least a portion thereof to lubricant-grade hydrocarbons, wherein said zeolite has an X-ray diffraction pattern substantially as set forth in Table I

TABLE I

| Interplanar spacings d(A°) | Relative Intensity I/Io |
|---|---|
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

10. The process of claim 9 wherein said zeolite consists essentially of acidic aluminosilicate.

11. A lubricant range hydrocarbon produced by process of any of claims 1 to 10, consisting essentially of aliphatics having a substantially linear structure C20+ and having a viscosity index of at least 85.

* * * * *